(12) United States Patent
Brown et al.

(10) Patent No.: US 11,680,933 B2
(45) Date of Patent: Jun. 20, 2023

(54) DETERMINATION OF SENSOR OPERATIONAL STATUS VIA SENSOR INTERROGATION

(71) Applicant: MSA TECHNOLOGY, LLC, Cranberry Township, PA (US)

(72) Inventors: Michael Alvin Brown, Cranberry Township, PA (US); Brian Keith Davis, Butler, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 359 days.

(21) Appl. No.: 16/585,684

(22) Filed: Sep. 27, 2019

(65) Prior Publication Data

US 2020/0103387 A1    Apr. 2, 2020

Related U.S. Application Data

(60) Provisional application No. 62/738,190, filed on Sep. 28, 2018.

(51) Int. Cl.
*G01N 33/00*    (2006.01)

(52) U.S. Cl.
CPC ..... *G01N 33/0031* (2013.01); *G01N 33/0006* (2013.01); *G01N 33/0073* (2013.01); *G01N 33/0016* (2013.01)

(58) Field of Classification Search
CPC ........... G01N 33/0031; G01N 33/0006; G01N 33/0073
See application file for complete search history.

(56) References Cited

U.S. PATENT DOCUMENTS

| 7,413,645 B2 | 8/2008 | Scheffler |
| 7,751,864 B2 * | 7/2010 | Buck, Jr. ............ A61B 5/14532 600/347 |

(Continued)

FOREIGN PATENT DOCUMENTS

| CN | 106662559 B | * | 9/2019 | ........ A61M 16/0003 |
| JP | 2014066530 A | * | 4/2014 | |

(Continued)

OTHER PUBLICATIONS

JP-2014066530-A-ENG (Year: 2014).*

(Continued)

*Primary Examiner* — Daniel S Larkin
*Assistant Examiner* — Fatemeh Esfandiari Nia
(74) *Attorney, Agent, or Firm* — Bartony & Associates LLC

(57) ABSTRACT

A method of operating a gas sensor for a gas analyte including a sensing component includes, in a first mode, interrogating the sensor by periodically applying an electrical signal to the sensing component of the sensor, measuring sensor response to the electrical signal which is indicative of a sensitivity of the sensor each time the electrical signal is applied to the sensing component, determining whether one or more thresholds have been exceeded based upon the sensor response determined each time the electrical signal is applied to the sensing component, and entering a second mode, different from the first mode in analysis of the sensor response to the periodically applied electrical signals, if one or more thresholds are exceeded.

24 Claims, 9 Drawing Sheets

(56) References Cited

U.S. PATENT DOCUMENTS

| | | | |
|---|---|---|---|
| 7,959,777 B2 | 6/2011 | Scheffler | |
| 9,528,957 B2 | 12/2016 | Scheffler | |
| 9,784,755 B2 | 10/2017 | Scheffler | |
| 10,234,412 B2 | 3/2019 | Swanson | |
| 2007/0251224 A1 | 11/2007 | Andrews | |
| 2008/0214910 A1* | 9/2008 | Buck | A61B 5/1495 600/310 |
| 2009/0137887 A1* | 5/2009 | Shariati | A61B 5/14542 600/345 |
| 2013/0186777 A1* | 7/2013 | Scheffler | G01N 33/497 205/785.5 |
| 2014/0273263 A1 | 9/2014 | Zanella, Sr. | |
| 2017/0160221 A1* | 6/2017 | Savoy | G01N 33/0008 |
| 2017/0184527 A1* | 6/2017 | Nogueira | G01N 33/48707 |
| 2017/0219515 A1 | 8/2017 | Davis | |
| 2018/0335411 A1 | 11/2018 | Zanella, Sr. | |
| 2018/0335412 A1 | 11/2018 | Zanella, Sr. | |
| 2019/0004020 A1* | 1/2019 | Dobrokhotov | G01N 25/34 |
| 2020/0386728 A1* | 12/2020 | Potyrailo | G01N 27/221 |

FOREIGN PATENT DOCUMENTS

| | | |
|---|---|---|
| WO | WO2018212965 | 11/2018 |
| WO | WO2018212966 | 11/2018 |
| WO | WO2020069317 | 4/2020 |

OTHER PUBLICATIONS

Cao, Z. and Stetter, J.R., "The Properties and Applications of Amperometric Gas Sensors," Electroanalysis, 4(3), 253-266 (1992).
International Search Report and Written opinion of counteraprt PCT International patent application No. PCT/US2019/053458.

* cited by examiner

DETERMINATION OF SENSOR OPERATIONAL STATUS VIA SENSOR INTERROGATION

CROSS-REFERENCE TO RELATED APPLICATIONS

This application claims benefit of U.S. Provisional Patent Application Ser. No. 62/738,190, filed Sep. 28, 2018, the disclosure of which is incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Gas sensors such as electrochemical sensors have been proven over many decades to be effective in detecting gases such as toxic gases in workplace environments. The low cost, speed of response and selectivity of, for example, electrochemical gas sensors are just a few of the characteristics that have made such sensors attractive for safety products. However, one of the necessary requirements for use electrochemical gas sensor and other gas sensors has been frequent calibration. For example, the sensitivity of an electrochemical sensor is influenced by the water content of its electrolyte, which changes over the seasons of the year, geographical location, etc. as a result of fluctuations in ambient relative humidity. Such relative humidity fluctuations lead to lower sensitivities in dry regions or during dry seasons and higher sensitivities in wetter region or during wetter seasons.

Prudence thus dictates that gas detection instrumentation, including electrochemical gas sensors and/or other gas sensors, be tested regularly for functionality. For example, frequent calibration with a test gas having a known concentration of the analyte or target gas (including a non-zero and zero concentrations) has been required to adjust for the sensitivity changes discussed above. It is a common practice to, for example, perform a "bump check," or functionality check on portable gas detection instrumentation on a daily basis. The purpose of this test is to ensure the functionality of the entire gas detection system, commonly referred to as an instrument. A periodic bump check or functionality check may also be performed on a permanent gas detection instrument to, for example, extend the period between full calibrations. Gas detection systems include at least one gas sensor, electronic circuitry (including a power supply) to drive the sensor, interpret its response and display its response to the user. The systems further include a housing to enclose and protect such components. A bump check typically includes: a) applying a test gas of interest (usually including a known concentration of the target or analyte gas the instrument is intended to detect or a simulant therefor to which the instrument is responsive); b) collecting and interpreting the sensor response; and c) indicating to the end user the functional state of the system (that is, whether or not the instrument is properly functioning).

In the past, bump tests were performed regularly and, typically, daily. Bump checks provide a relatively high degree of assurance to the user that the gas detection device is working properly. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any protection and/or diffusion membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is being interpreted properly. Moreover, the bump check ensures that the indicator(s) or user interface(s) (for example, a display and/or an annunciation functionality) of the gas detection instrument is/are functioning as intended.

However, periodic/daily bump checks have a number of significant drawbacks. For example, such bump checks are time consuming, especially in facilities such as industrial facilities that include many gas detection systems or instruments. The bump check also requires the use of expensive and potentially hazardous calibration or test gases. Further, the bump check also requires a specialized gas delivery system, usually including a pressurized gas bottle, a pressure reducing regulator, and tubing and adapters to correctly supply the calibration or test gas to the instrument. The requirement of a specialized gas delivery system often means that the opportunity to bump check a personal gas detection device is limited in place and time by the availability of the gas delivery equipment.

Recently, a number of systems and methods have been proposed to reduce the number of bump tests required. Such a system may, for example, include electronic interrogation of a sensor in the absence of a test gas. The fluctuations in sensitivity of an electrochemical gas sensor arising from moisture loss or gain in a number of sensors occurs gradually but in a predictable manner as the average relative humidity slowly changes. Likewise, the sensor response to an electronic interrogation (in the absence of or without application of a test gas including a known concentration of the analyte gas or a substitute therefor) changes in a similar manner. An electronic interrogation may, for example, be used to measure sensitivity changes and correct for them. Such electronic interrogation techniques and resulting corrections for electrochemical gas sensors are, for example, disclosed in U.S. Pat. Nos. 7,413,645, 7,959,777, 9,784,755, and 9,528,957, and in U.S. Patent Application Publication Nos. 2013/0186777 and 2017/0219515, the disclosures of which are incorporated herein by reference. In such electronic interrogation approaches, an electrical signal such as a potential pulse is typically applied to a sensing element or component of the sensor and the resulting response is measured and recorded. A response may, for example, be measured in the form of, for example, a maximum peak (current) value (MPV) or and/or another parameter. These responses are compared to values taken during a previous gas test/pulse cycle. Changes from the calibration values may be correlated to changes in sensor sensitivity.

Various electronic interrogation techniques have also been developed for sensors other than electrochemical sensors (such as combustible gas sensors). For example, U.S. Patent Application Publication No. 2014/0273263, the disclosure of which is incorporated herein by reference, discloses periodic measurement of a variable related to reactance of a sensing element of a combustible gas sensor to determine the operational status of the sensing element. U.S.

patent application Ser. Nos. 15/597,933 and 15/597,859 disclose electronic interrogation techniques for combustible gas sensors in which a variable related to the mass of a sensing element (for example, an electrical property such as resistance) is periodically measured to determine if, for example, substances such as inhibitors or poisons have been deposited on the sensing element.

Although, current testing or interrogation techniques are valuable in determining if an individual sensor is in a functional state of operation at the time of testing, relatively little success has been achieved in predicting future failure of such sensors.

SUMMARY

In one aspect, a method of operating a gas sensor for a gas analyte including a sensing component includes, in a first mode, interrogating the sensor by periodically applying an electrical signal to the sensing component of the sensor, measuring sensor response to the electrical signal which is indicative of a sensitivity of the sensor each time the electrical signal is applied to the sensing component, determining whether one or more thresholds have been exceeded based upon the sensor response determined each time the electrical signal is applied to the sensing component, and entering a second mode, different from the first mode in analysis of the sensor response to the periodically applied electrical signals, if one or more thresholds are exceeded.

In a number of embodiments, the sensor response to the periodically applied electrical signals in the second mode is analyzed to determine if the sensor response to the periodically applied electrical signals is stabilizing. The method may, for example, further including determining a rate of change of the sensor response during the second mode to determine if the sensor response to the periodically applied electrical signals is stabilizing. In a number of embodiments, at least one of a magnitude and a direction of the rate of change of the sensor response is determined. In a number of embodiments, the method further includes changing the one or more thresholds after determining that the sensor response to the periodically applied electrical signals has stabilized. There is no need to apply any test gas during electronic sensor interrogation. In that regard, the sensor response may be determined without application of a test gas to the sensor. In a number of embodiments, at least one of a magnitude and a direction of the rate of change of the sensor response is determined.

The sensor may, for example, be an electrochemical gas sensor and the sensing component may, for example, be a working electrode of the electrochemical gas sensor. A value for the sensor response may, for example, be determined on the basis of at least one defined parameter of the sensor response. In a number of embodiments, the at least one defined parameter of the sensor response is selected from the group of a maximum current peak value, an area under a current curve, a minimum peak value, a peak-to-peak value, a reverse area under the curve, a baseline value of the sensor response or functions or one or more thereof (for example, products, ratios or more complex functions of one or more of such parameters). The value for the sensor response at each of the periodically applied electronic interrogations may, for example, be a change in the value at least one defined parameter of the sensor response measure at each of the periodically applied electronic interrogations from a value thereof determined at a calibration of the sensor.

In a number of embodiments, the one or more threshold values for the sensor response are determined by tracking a value of the sensor response over time and determining an upper threshold and a lower threshold of nominal behavior for the sensor. In a number of embodiments, the one or more threshold values for the sensor response are determined by tracking the sensor response over time for a plurality of like sensors and determining a group upper threshold and a group lower threshold of nominal behavior for the plurality of sensors. In a number of embodiments in which group thresholds are determined, one or more other threshold values are determined by tracking the sensor response of each of the plurality of like sensors over time and determining an individual upper threshold and an individual lower threshold of nominal behavior for each of the plurality of like sensors. The second mode may, for example, be entered for each of the plurality of like sensors based upon a comparison the sensor response of each of the plurality of like sensors to the group upper threshold and the group lower threshold as well as to the individual upper threshold and the individual lower threshold.

The sensors of the plurality of like sensors hereof may, for example, exhibit at least one common characteristic other than being a like sensor. The at least one common characteristic may, for example, be a geographical area of deployment or a range of time of manufacture. Groups and subgroups of like sensor may be established in a number of embodiments.

In a number of embodiments, data from the sensor is transmitted to a remote processor system for processing and/or analysis. In a number of embodiments, data or information from a second gas sensor for a second gas analyte different from the gas analyte or data from a third sensor for an environmental condition is transmitted to the gas sensor.

In another aspect, a system includes a sensor including a sensing component having at least one property sensitive to an analyte, and circuitry in operative connection with the sensing component. The circuitry is configured, in a first mode, to interrogate the sensor by periodically applying an electrical signal to the sensing component, measuring a sensor response to the electrical signal which is indicative of a sensitivity of the sensor each time the electrical signal is applied to the sensing component, and compare the sensor response to one or more threshold values. The circuitry is further configured to determine, based upon the comparison of sensor response to the one or more threshold values, whether to enter a second mode, different from the first mode in analysis of sensor response to the periodically applied electrical signals, if one or more thresholds are exceeded.

In a number of embodiments, the circuitry is configured to analyze the sensor response to the periodically applied electrical signals in the second mode to determine if the sensor response to the periodically applied electrical signals is stabilizing. The circuitry may, for example, be further configured to determine a rate of change of the sensor response during the second mode to determine if the sensor response to the periodically applied electrical signals is stabilizing. At least one of a magnitude and a direction of the rate of change of the sensor response may, for example, be determined. In a number of embodiments, the circuitry is further configured to change the one or more thresholds after determining that the sensor response to the periodically applied electrical signals has stabilized. The circuitry may, for example, be configured to determine the sensor response without application of a test gas to the sensor.

In a number of embodiments, the sensor is an electrochemical gas sensor and the sensing component is a working electrode of the electrochemical gas sensor. As described above, a value for the sensor response is determined on the basis of at least one defined parameter of the sensor response. In a number of embodiments, the at least one defined parameter of the sensor response is selected from the group of a maximum current peak value, an area under a current curve, a minimum peak value, a peak-to-peak value, a reverse area under the curve, a baseline value of the sensor response, or a function or functions of one or more thereof described above. The value for the sensor response at each of the periodically applied electronic interrogations may, for example, be a change in the value at least one defined parameter of the sensor response measure at each of the periodically applied electronic interrogations from a value thereof determined at a calibration of the sensor.

In a number of embodiments, the one or more threshold values for the sensor response are determined by tracking a value of the sensor response over time and determining an upper threshold and a lower threshold of nominal behavior for the sensor. In a number of embodiments, the one or more threshold values for the sensor response are determined by tracking the sensor response over time for a plurality of like sensors and determining a group upper threshold and a group lower threshold of nominal behavior for the plurality of sensors. Each of the plurality of like sensors may, for example, include a communication system to transmit data regarding the sensor response to the periodically applied electronic interrogations and to receive data regarding the group upper threshold and the group lower threshold of nominal behavior for the plurality of sensors. In a number of embodiments wherein group thresholds are determined, one or more other threshold values are determined by tracking the sensor response of each of the plurality of like sensors over time and determining an individual upper threshold and an individual lower threshold of nominal behavior for each of the plurality of like sensors. The second mode may, for example, be entered for each of the plurality of like sensors based upon a comparison the sensor response of each of the plurality of like sensors to the group upper threshold and the group lower threshold as well as to the individual upper threshold and the individual lower threshold.

In a number of embodiments in which a plurality of like sensors are tracked, each of the plurality of like sensors has at least one common characteristic other than being a like sensor. The at least one common characteristic may, for example, be a geographical area of deployment or a range of time of manufacture.

Data from the sensor(s) may, for example, be transmitted to a remote processor system for processing and/or analysis. Data or information from a second gas sensor for a second gas analyte different from the gas analyte or data from a third sensor for an environmental condition is transmitted to the gas sensor.

In a further aspect, a method of operating a system including a plurality of like gas sensors, wherein each of the plurality of like gas sensors includes a sensing component, includes, in a first mode, interrogating each of the plurality of like gas sensors by periodically applying an electrical signal to the sensing component of the sensor, determining a sensor response to the electrical signal which is indicative of a sensitivity for each of the plurality of like gas sensors each time the electrical signal is applied to the sensing component thereof, and analyzing the sensor response of each of the plurality of like gas sensors to the periodically applied electrical signals based upon a nominal response of the plurality of like gas sensors to the periodically applied electrical signals determined over time. The method may, for example, further include determining whether to enter a second mode, different from the first mode in analysis of the sensor response to the periodically applied electrical signals, for each of the plurality of like gas sensors based upon comparison of the sensor response of each of the plurality of like gas sensors to the nominal response of the plurality of like gas sensors in the first mode. The method may be further characterized as described above.

In still a further aspect, a system includes a plurality of like gas sensors, wherein each of the plurality of like gas sensors includes a sensing component and electronic circuitry in operative connection with the sensing component. The electronic circuitry is configured, in a first mode, to interrogate each of the plurality of like gas sensors by periodically applying an electrical signal to the sensing component of the sensor, to determine a sensor response to the electrical signal which is indicative of a sensitivity for each of the plurality of like gas sensors each time the electrical signal is applied to the sensing component thereof, and to analyze the sensor response to the periodically applied electrical signals based upon a nominal response of the plurality of like gas sensors to the periodically applied electrical signals determined over time. The electronic circuitry of each of the plurality of like sensors may, for example, be further configured to determine whether to enter a second mode, different from the first mode in analysis of the sensor response to the periodically applied electrical signals, based upon comparison of the sensor response to the nominal response of the plurality of like gas sensors in the first mode. The system may be further characterized as described above.

The present devices, systems, and methods, along with the attributes and attendant advantages thereof, will best be appreciated and understood in view of the following detailed description taken in conjunction with the accompanying drawings.

DETAILED DESCRIPTION

Figure 1A:
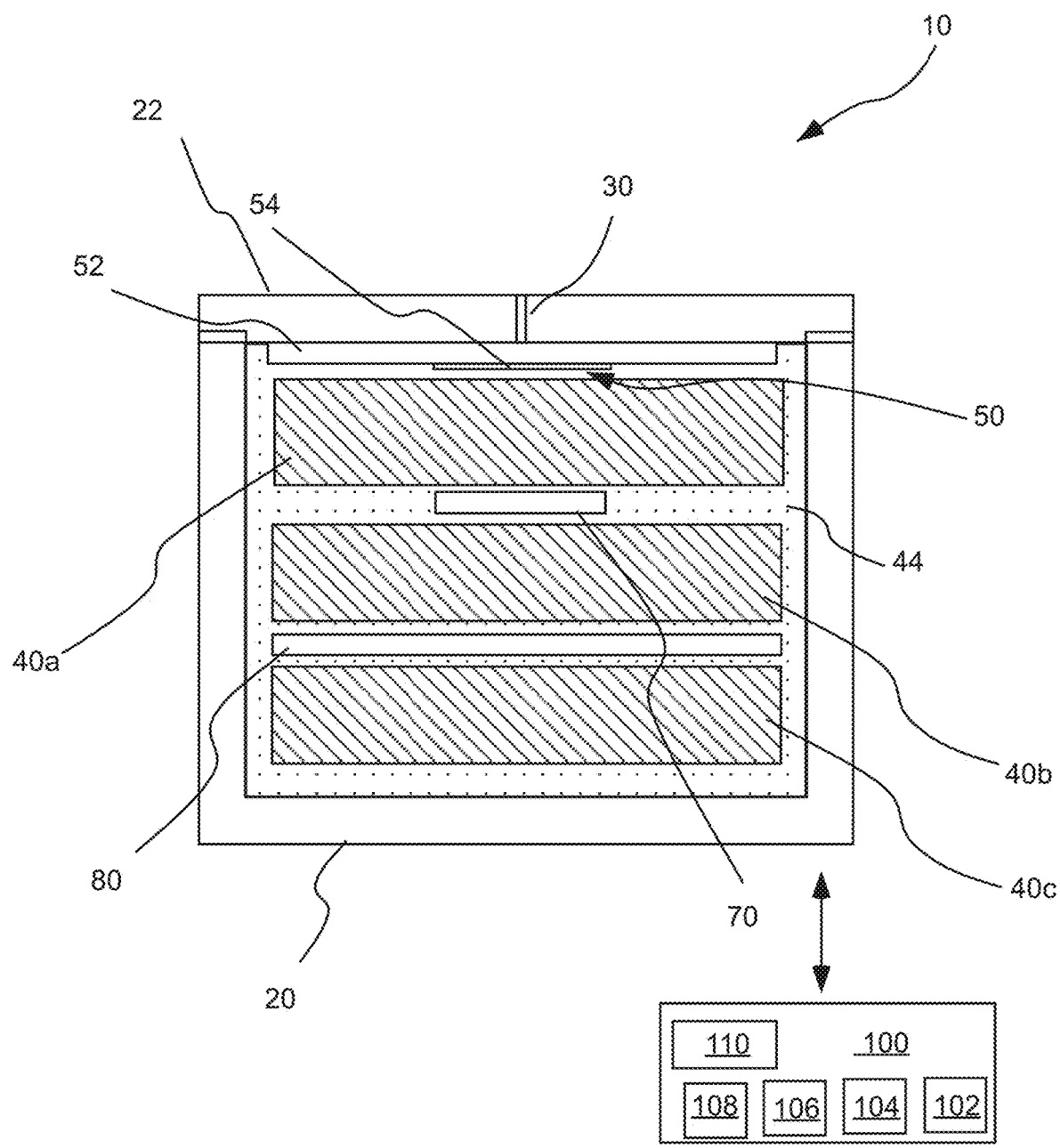
FIG. 1A illustrates schematically an embodiment of an electrochemical sensor hereof.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "processor" includes a plurality of such processors and equivalents thereof known to those skilled in the art, and so forth, and reference to "the processor" is a reference to one or more such processors and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "logic," as used herein includes, but is not limited to. hardware, firmware, software or combinations thereof to perform a function(s) or an action(s), or to cause a function or action from another element or component. Based on a certain application or need, logic may, for example, include a software controlled microprocess, discrete logic such as an application specific integrated circuit (ASIC), or other programmed logic device. Logic may also be fully embodied as software. As used herein, the term "logic" is considered synonymous with the term "circuit."

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

A number of embodiments hereof are discussed in connection with electrochemical gas sensors and electronic interrogation thereof. However, the devices, systems and methods hereof are applicable to any type of sensor in which diagnostic testing or electronic interrogation of a sensing component is performed.

As described above, recent development for electronic interrogation of electrochemical sensors have diminished the requirement for frequent calibrations with test gas. In an electronic interrogation, an electrical signal is applied to a sensing component of the sensor which interacts with the target or analyte gas. For example, an electrical signal may be applied to a working electrode of an electrochemical sensor which includes an electrocatalyst which catalyzes a reduction or oxidation reaction with the analyte gas. Likewise, an electrical signal may be applied to a sensing element of a combustible gas sensor which may or may not include a catalyst which facilitates combustion of an analyte gas (for example, by providing a reaction pathway with a lower activation energy than a non-catalyzed reaction) upon heating of the sensing element to a suitable temperature.

In the case of electrochemical gas sensors, electronic interrogations may, for example, be of fairly short duration to minimize the amount of time a sensor is offline to conduct sensor testing diagnostics (that is, during a sensor electronic interrogation cycle). In a number of representative embodiments of, for example, electrochemical gas sensor devices, systems and/or methods for electronic interrogation may allow for a return to a normal (gas sensing) mode operation for the electrochemical sensors hereof that is under 10 seconds, under 5 seconds or even under 1 second. The devices, systems and methods for electronic interrogation of sensor not only allow an instrument including one or more sensors to remain "online", but also provide for active, automatic sensor status monitoring as a background operation, without the requirement of user initiation. The electronic interrogations hereof occur periodically. As used herein, the term periodically refers to electronic interrogation which occur from time to time or multiple times over time but not necessarily at a fixed interval or frequency. The frequency of the electronic interrogations may be constant or may vary. Providing for sensor interrogation at a frequency of, for example, several times an hour can provide for nearly constant sensor life and health status monitoring.

In an electrochemical gas sensor, the gas to be measured typically passes from the surrounding atmosphere or environment into a sensor housing through a gas porous or gas permeable membrane to a first electrode or working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working electrode. A comprehensive discussion of electrochemical gas sensors is also provided in Cao, Z. and Stetter, J. R., "The Properties and Applications of Amperometric Gas Sensors," *Electroanalysis*, 4(3), 253 (1992), the disclosure of which is incorporated herein by reference.

The working and counter electrode combination produces an electrical signal that is (1) related to the concentration of the analyte gas and (2) sufficiently strong to provide a signal-to-noise ratio suitable to distinguish between concentration levels of the analyte gas over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte.

Electrical connection between the working electrode and the counter electrode is maintained through the electrolyte. Functions of the electrolyte include: (1) to efficiently carry the ionic current; (2) to solubilize the analyte gas; (3) to support both the counter and the working electrode reactions; and (4) to form a stable reference potential with the reference electrode. Criteria for an electrolyte may, for example, include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction (a redox) reaction occurs to provide a mechanism whereby the ionic conduction of the electrolyte solution is coupled with the electron conduction of the electrode to provide a complete circuit for a current. The measurable current arising from the cell reactions of the electrochemical cell is directly proportional to the extent of reaction occurring at the electrode. Preferably, therefore, a high reaction rate is maintained in the electrochemical cell. For this reason, the counter electrode and/or the working electrode of the electrochemical cell generally include an appropriate electrocatalyst on the surface thereof to support the reaction rate.

As a result of electrostatic forces, the volume of solution very close to the working electrode surface is a very highly ordered structure. This structure is important to understanding electrode processes. The volume of solution very close to the electrode surface is variously referred to as the diffusion layer, diffuse layer, and or the Helmholtz layer or plane.

The magnitudes of the resistance and capacitance present in an electrochemical cell are a result of the nature and identities of the materials used in its fabrication. The resistance of the electrolyte is a result of the number and types of ions dissolved in the solvent. The capacitance of the electrode is primarily a function of the effective surface area of the electrocatalyst. In an ideal world, these quantities are invariant. However, the solution resistance present in an amperometric gas sensor that utilizes an aqueous (water-based) electrolyte may change, for example, as a result of exposure to different ambient relative humidity levels. As water transpires from the sensor, the chemical concentration of the ionic electrolyte increases. This concentration change can lead to increases or decreases in the resistivity of the electrolyte, depending on the actual electrolyte used.

Moreover, even for substances normally thought of as insoluble in a particular solvent, there is a small, but finite concentration of the substance in the solvent. For example, there is a very small, but finite concentration of metal from the electrodes dissolved in the electrolyte of an electrochemical sensor. This small concentration of dissolved metal is constantly in flux. That is, metal atoms are constantly dissolving from the electrode and then replating somewhere else. The net effect of this process is to decrease the effective surface area of the electrode. This has the effect of lowering the sensor capacitance over time. Both of the above-described effects have the net effect of changing the sensitivity of the sensor over its lifetime.

FIG. 1A illustrates a schematic diagram of a representative embodiment of an electrochemical sensor 10 which may be used in the devices, systems and methods hereof. Sensor 10 includes a housing 20 having a gas inlet 30 for entry of one or more target gases or analyte gases into sensor 10. In the illustrated embodiment, electrolyte saturated wick materials 40a, 40b and 40c separate a working electrode 50 from a reference electrode 70 and a counter electrode 80 within sensor 10 and/or provide ionic conduction therebetween via the electrolyte 44 within housing 20 and absorbed within wick materials 40a, 40b and 40c. Electronic circuitry 100 as known in the art is provided, for example, to maintain a desired potential difference between working electrode 50 and reference electrode 70, to vary or pulse the potential difference as described herein, and to process an output signal from sensor 10.

In the illustrated embodiment, working electrode 50 may be formed by, for example, depositing a first layer of catalyst 54 on a diffusion membrane 52 (using, for example, catalyst deposition techniques known in the sensor arts). Gas readily transfers or transports (via, for example, diffusion) through diffusion membrane 52, but electrolyte 44 does not readily transfer or transport therethrough. Working electrode 50 may be attached (for example, via heat sealing) to an inner surface of a top, cap or lid 22 of housing 20.

Electronic circuitry 100 may, for example, include a processor or controller system 102 including one or more processors or microprocessors to control various aspects of the operation of sensor 10. A memory system 104 may be placed in operative or communicative connection with processor system 102 and may store software for control of sensor 10 and/or analysis of the output thereof as described herein. A user interface system (including, for example, a display, speaker etc.) may also be placed in operative or communicative connection with processor system 102. A communication system 108 such as a transceiver may be placed in operative or communicative connection with processor system 102 for wired and/or wireless communication. A power source 110 (for example, a battery system) may provide power for electronic circuitry 100.

Figure 1B:
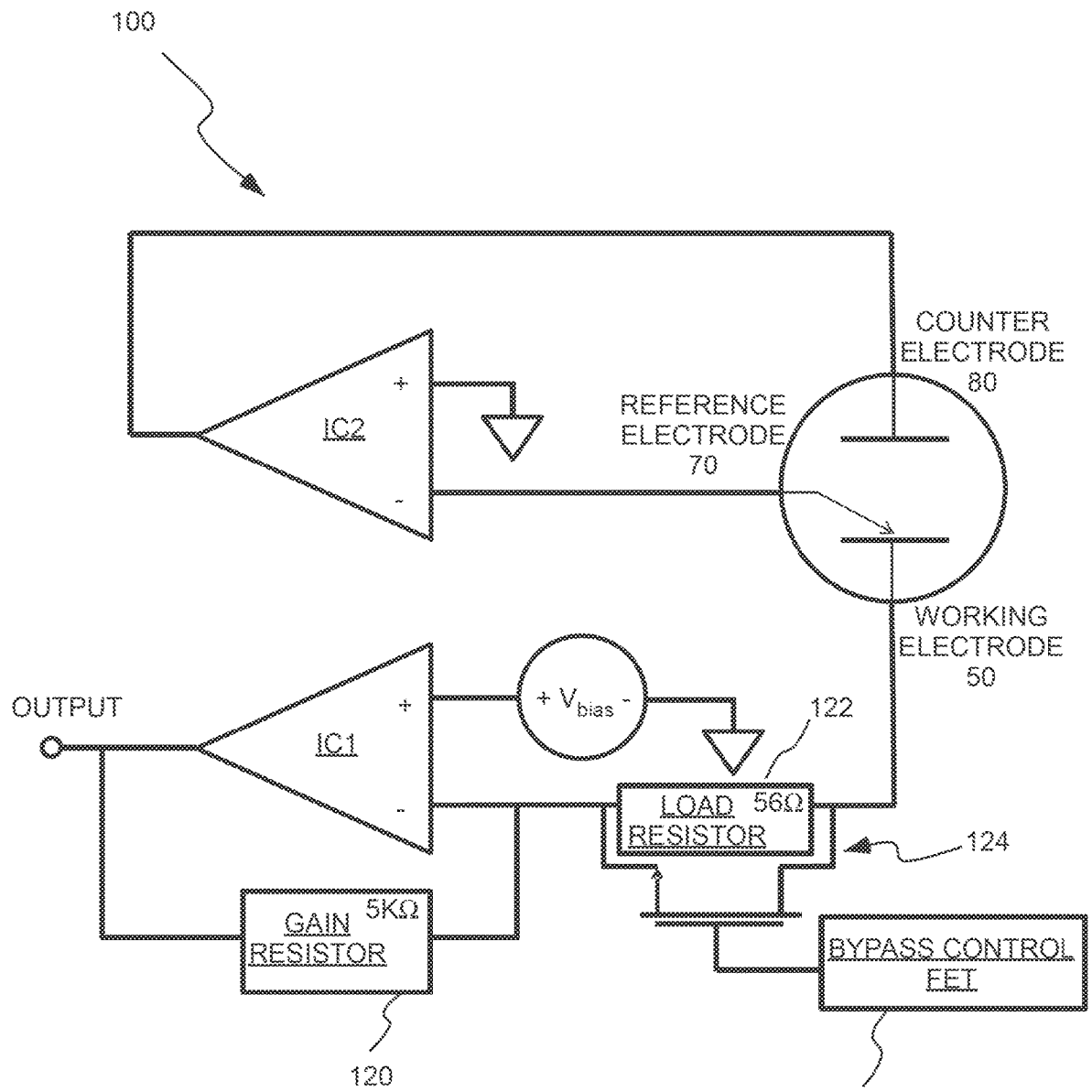
FIG. 1B illustrates a schematic circuit diagram of an embodiment of a sensor hereof.

FIG. 1B illustrates schematically an embodiment of a portion or part of electronic or control circuitry 100 used in a number of studies of the sensors hereof. The portion of electronic circuitry 100 illustrated in FIG. 1B is sometimes referred to as a potentiostatic circuit. In a three-electrode sensor as illustrated in FIG. 1A, a predetermined potential difference or voltage is maintained between reference electrode 70 and sensing or working electrode 50 to control the electrochemical reaction and to deliver an output signal proportional to the current produced by the sensor. As described above, working electrode 50 responds to the analyte or target gas by either oxidizing or reducing the gas. The redox reaction creates a current flow that is proportional to the gas concentration. Current is supplied to sensor 10 through counter electrode 80. A redox reaction opposite to that of the reaction at the working electrode takes place at counter electrode 80, completing the circuit with working electrode 50. The potential of counter electrode 80 is allowed to float. When gas is detected, the cell current rises and counter electrode 80 polarizes with respect to reference electrode 70. The potential on counter electrode 80 is not important, as long as the circuit provides sufficient voltage and current to maintain the correct potential of working electrode 50.

As, for example, described in U.S Patent Application Publication No. 2017/0219515, in a number of representative embodiments, the measuring circuit for electrical/electronic circuitry 100 includes a single stage operational amplifier or op amp IC1. The sensor current is reflected across a gain resistor 120 (having a resistance of 5 kΩ in the illustrated embodiment), generating an output voltage. A load resistor 122 (having a resistance of 56Ω in the illustrated embodiment) may be chosen, for example, via a balance between the fastest response time and best signal-to-noise ratio.

A control operational amplifier IC2 provides the potentiostatic control and provides the current to counter electrode 80 to balance the current required by working electrode 50. The inverting input into IC2 is connected to the reference electrode but does not draw any significant current from the reference electrode.

During electronic interrogation of an electrochemical gas sensor hereof such as sensor 10, a non-faradaic current may be induced (for example, via application of energy to working electrode 50). For example, an electrical signal may be applied to working electrode 50 such that a step change in potential is created which generates a non-faradaic current. The generated non-faradaic current can be used to monitor the sensor operational status, functionality or health as a result of the charging of the electrodes. However, as described above, the sensor is subsequently returned to its normal bias potential or potential range for normal operation in sensing a target or analyte gas. The process of returning the sensor to its operating bias or operating potential difference (which may be zero) produces a current peak (a charge build-up) in the opposite direction. The current peak arising on return to the operating potential difference can take many seconds to dissipate.

Information regarding sensor health, operational status or operational state may be obtained from a response to an electronic interrogation measured in the form of, for example, (i) a maximum peak value (MPV), which is the maximum current observed upon the application of the potential pulse; (ii) an area under the curve (AUC), which is the integrated current response of the working electrode after the application of the potential pulse (this is equivalent to the charging response of the sensor; (iii) minimum peak value (mPV), which is the minimum current obtained upon removal or reversal of the potential pulse, ordinarily as the difference in current observed immediately after and immediately before the removal or reversal of the potential pulse, though it can also be tabulated and used as the difference between the minimum current and the baseline; (iv) peak-to-peak value (PP), which is the algebraic difference between the maximum and minimum observed currents; (v) reverse area under the curve (rAUC), or, more accurately, the area under the reverse curve, which is the charging current obtained by integrating the current response after the removal or reversal of the potential pulse; (vi) change in a baseline or baseline output and functions thereof (for example, products, ratios and/or more complex functions of one, two or more such parameters). The operational state of a sensing component (for example, a working electrode of an electrochemical gas sensor or a sensing element of a combustible gas sensor) and the sensor/sensor device is typically determined by relating such parameters and/or other parameters to changes in sensitivity of the sensor. Sensitivity refers to the ratio of the output signal (for example, current) and the physical quantity measured (for example, concentration of analyte or target gas).

Figure 1C:
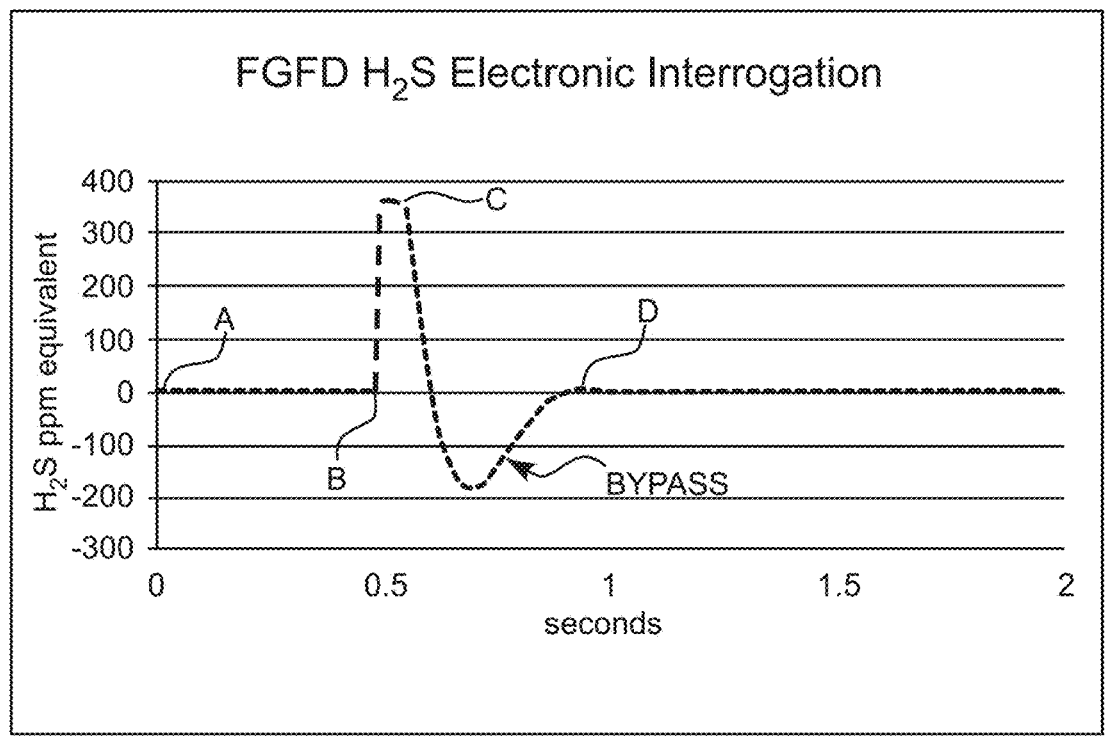
FIG. 1C illustrates a representative response to an electronic interrogation of an electrochemical gas sensor.
Figure 1D:
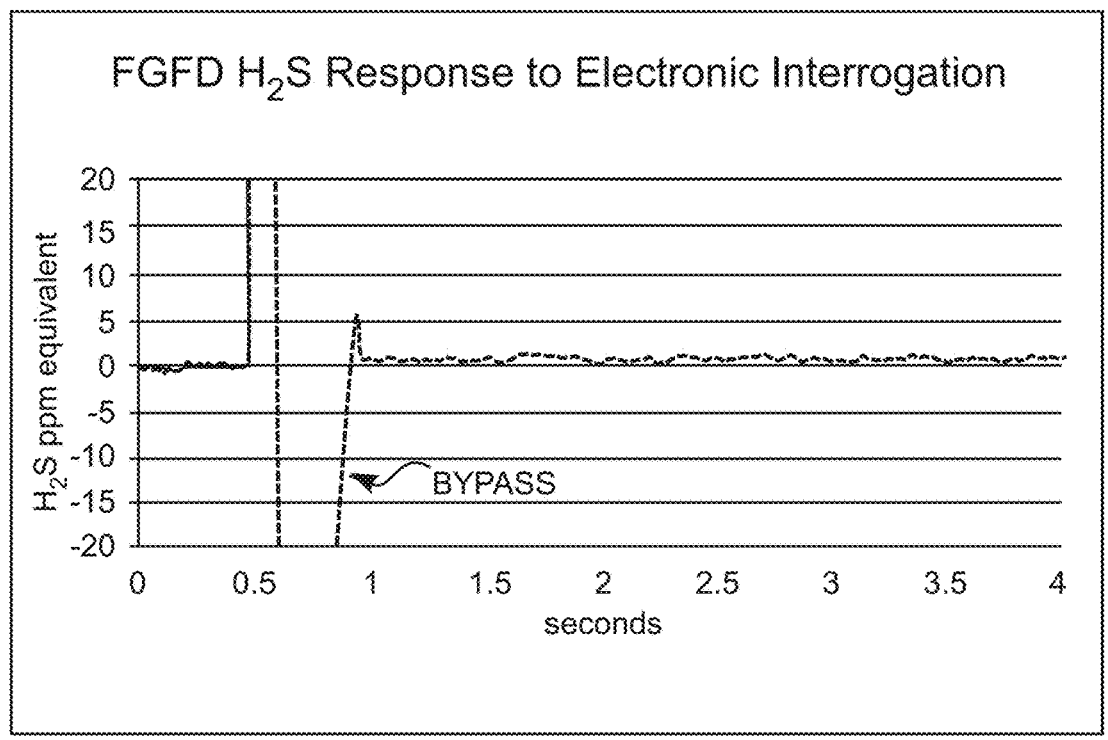
FIG. 1D illustrates the response of FIG. 1C with an enlarged scale.

Measuring/analyzing single data points or multiple data points over short time spans provides a response/current versus time curve as, for example illustrated in FIGS. 1C and 1D for a representative electrochemical gas sensor for hydrogen sulfide or $H_2S$. A rapid discharge of even relatively large current peaks arising when inducing a non-faradaic current in sensor 10 (or another sensor hereof) and/or in returning sensor 10 (or another sensor hereof) to its operating potential difference may be achieved via active control of sensor electronic circuitry or electronics 100 (for example, by decreasing a load resistance in electronic circuitry 100 between working electrode 50 and the point at which the output/response is measured after the test potential difference has been applied). In a number of embodiments, the load resistance between working electrode 50 and the output of operational amplifier IC1 is decreased to a low value. Subsequently, the load resistance between working electrode 50 and the output of operational amplifier IC1 is restored to its normal or operational load resistance (or to within an operation range of load resistance) after the charge is substantially dissipated or fully dissipated.

In a number of embodiments, load resistor 122 (see FIG. 1B) is bypassed to decrease the load resistance between working electrode 50 and the inverting terminal of operational amplifier IC1. A bypass circuit 124 may, for example, be provided to bypass load resistor 122. In a number of embodiments, a field effect transistor (FET) 126 was used as a switch in a bypass circuit 124 to controllably effect a bypass or short circuit around load resistor 122. In a number of embodiments, a metal-oxide-semiconductor FET or MOSFET was used.

FIGS. 1C and 1D illustrate the output of a representative sensor 10 including a working electrode 50 designed to detect hydrogen sulfide or $H_2S$. In the studied embodiment of FIGS. 1C and 1D, working electrode 50 was formed by depositing an iridium catalyst on a diffusion membrane, reference electrode 70 was formed by depositing an iridium catalyst on a diffusion membrane, and counter electrode 80 was formed by depositing an iridium catalyst on a diffusion membrane. The bias potential or operating potential difference of the sensor was 0 mV. As illustrated in FIG. 1C, at a time represented by point A, an electronic interrogation procedure is initiated. After 0.5 seconds (represented by point B), a test potential difference is applied. In the illustrated studies, a test potential of +10 mV was applied. A maximum peak value (MPV) of output was recorded $1/16^{th}$ of a second after application of the test potential as represented by point C. At that time, the potential was also returned to the operating potential difference of 0 mV. In bypassing load resistor 122, FET 126 was activated at generally the same time or contemporaneously with return of the potential to the operating potential difference. The significantly lower load resistance causes a significant negative current spike (which would be viewed as a very high negative gas ppm reading in the normal mode of operation). However, the rapid discharge which occurs upon bypassing load resistor 122 returns the sensor output to the baseline in a very short period of time (that is, in less than 1 second). The scale is expanded in FIG. 1D to better illustrates this result. It, however, takes many seconds for the output to return to the baseline output when load resistor 122 is not bypassed. As illustrated in FIG. 1C, when FET 126 is deactivated and 56Ω load resistor 122 is restored in the circuit at a time of approximately 0.95 seconds as represented by point D, the output current is below a value that would be discerned by the end user. This value is typically in the range of approximately 0 to ±2 ppm of the target gas Information regarding sensor health or the state of the sensor may be obtained maximum peak (current) value (MPV) and/or another parameter as described above upon application of an electrical signal in, for example, the form of an electrode potential change that is quite small and/or short in duration, and measuring/analyzing single data points or multiple data points over short time spans in a resultant response/current curve. In a number of representative embodiments hereof, MPV is used to characterize the sensing element/working electrode of an electrochemical sensor. As described above, a rapid discharge of even relatively large current peaks arising when inducing a non-faradaic current in sensor 10 (or another electrochemical sensor hereof) and/or in returning sensor 10 (or another sensor hereof) to its operating potential difference may be achieved via active control of sensor electronics/electronic circuitry 100 (for example, by decreasing a load resistance in electronic circuitry 100 between working electrode 50 and the point at which the output/response is measured after the test potential difference has been applied). In a number of embodiments, the load resistance between working electrode 50 and the output of operational amplifier IC1 is decreased to a low value. Subsequently, the load resistance between working electrode 50 and the output of operational amplifier IC1 is restored to its normal or operational load resistance (or to within an operation range of load resistance) after the charge is substantially dissipated or fully dissipated.

The fluctuations in sensitivity of an electrochemical sensor as a result of, for example, moisture loss or gain occur gradually, but in a generally predictable manner, as the average relative humidity slowly changes. The sensor response to a gas-less, electronic interrogation such as described above changes in a similar manner. Electronic interrogation may be used to track sensitivity changes and to correct for sensitivity changes as described in, for example, U.S. Pat. Nos. 7,413,645, 7,959,777, 9,784,755, and 9,528, 957, and in U.S. Patent Application Publication Nos. 2013/0186777 and 2017/0219515. As described above, a potential pulse is typically applied to the sensing component of the sensor and the resulting response is recorded, for example, in the form of a maximum peak (current) value and/or one or more other parameters. These responses may be compared to values taken during a previous gas test/pulse cycle. Changes from calibration values are correlated to changes in operational status/sensor sensitivity. In this way, a sensor's health at the time of interrogation is evaluated. The sensitivity may then be adjusted to correct for such changes. Such methodologies provide a real-time status of the sensor's health at the time of the interrogation but do not address future sensor performance.

In a number of embodiments of devices, systems and methods hereof multiple, consecutive interrogation events are performed in a first mode or first interrogation mode to, for example, determine if a sensor response to the electronic interrogation is outside of nominal behavior. For example, changes in value one or more variables based upon or determined from one or more parameters such as MPV, AUC and/or other parameters may be used to evaluate when a sensor is need of further/altered analysis and/or maintenance. If, for example, a sensor's response to interrogation is outside of a nominal, normal or expected variation (for example, expected variation as a result of normal, gradual changes in relative humidity), that sensor may be identified or flagged as needing attention.

In a number of embodiments hereof, once a sensor exhibits a response to an electronic interrogation that is outside of a nominal range of response, a second mode, second interrogation mode or observe mode is entered. In the second mode, analysis of the response of the sensor to electronic interrogation is different than in the first mode. The sampling rate of one or more parameters may be altered and/or the identity of the one or more parameters measured may change in the second mode. In a number of embodiments, a determination is made over one or more periods of time in the second mode from the measured response to periodic electronic interrogations (that is, multiple electronic interrogations over time) if the response of the sensor to the electronic interrogations is stable or stabilizing. It may, for example, be determined over one or more periods of times in the second mode whether the sensor response is approaching an average rate of change within a defined threshold or remaining within a determined or defined range of response over the one or more periods of time in the second mode. In a number of embodiments, a rate of change in a measured variable (based upon or derived from one or more parameters) may, for example, be determined over one or more periods of time in the second mode to determine if the sensor response is stabilizing. A determination regarding sensor response stability (for example, as determined from a magnitude/direction of a rate of change over one or more periods of time in the second mode) may be used to determine, for example, if sensor setting should be changed (for example, changing nominal response range, changing sensitivity compensation; etc.), if a recalibration of the sensor is needed or if the sensor needs to be replaced. In the devices, systems and methods hereof, a sensor's health or operational status (that is, sensitivity) is not only gauged at the instant of the electronic interrogation, its future health is estimated using an aggregate of health measurements (that is, measured responses to electronic interrogations).

The nominal range of sensor response to electronic interrogation may be derived in a number of ways. A straightforward manner of determining the nominal range of response is to track the response of the sensor over a period of time to determine nominal or normal variation. Limits (for example, an upper threshold and a lower threshold) may then be set to identify or flag deviations in sensor behavior. Such limits may, for example, be redetermined over time as further electronic interrogations are carried out. The nominal limits or thresholds and whether such nominal limits have been exceeded (thereby triggering entry of the second mode) hereof may, for example, be determined via software stored in memory system 104 and executable by processor system 102. An example is displayed in FIG. 2, wherein the change in MPV value from the initial calibration point (at time of manufacture) is plotted over 80+ days.

Figure 2:
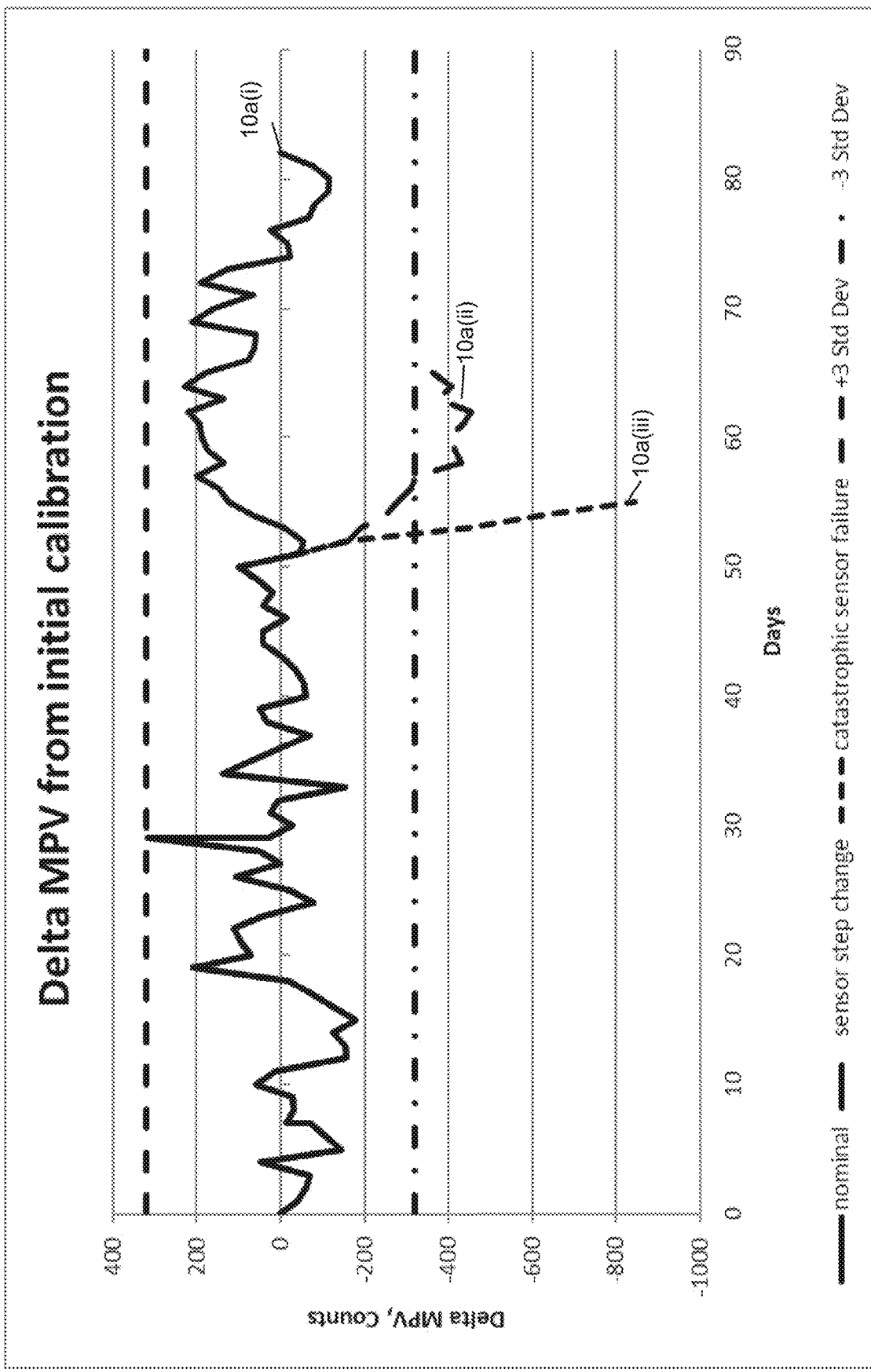
FIG. 2 illustrates a change, after initial calibration, in sensor response (a maximum peak (current) value or MPV) to electronic interrogations over time.

In FIG. 2, a sensor exhibiting the nominal behavior is labeled sensor 10a(i). The average over the 80+ days of the study of FIG. 2 is 26 counts with a standard deviation of 107 counts. Limits or thresholds may, for example, be established using, a multiple of the standard deviation (for example, between ±1 to ±3 sigma). In the illustrated embodiment, limits were established using ±3 times the standard deviation to capture 99.7% of the nominal distribution. Such limits (upper and lower thresholds) are denoted by the upper and lower dashed traces in FIG. 2. In a first mode as described above, delta MPV is tracked over time and compared to the nominal delta MPV values (that is, the upper and lower thresholds of nominal delta MPV values). Once the delta MPV moves beyond one of those limits, the system may, for example, enter the second mode or observe mode wherein analysis of the response of the electronic interrogation is different than in the first mode. As described above, the rate of change of the delta MPV may be tracked over one or more time periods in the second mode to determine if the sensor response to the electronic interrogations is stabilizing. Thus, in a number of embodiments of the second mode, electronic interrogation continues as described above and the delta MPV is still tracked, but the rate of change of the delta MPV (dΔMPV/dt) is also tracked.

Two representative examples of tracking the rate of change of the delta MPV are illustrated in FIG. 2. The data trace of sensor 10a(ii) indicates that the sensor has experienced a step change in MPV value. Once the delta MPV has moved beyond the −3 sigma value/limit, the rate of change is monitored in the second mode of operation as described above. Further, an alert or notification may (but need not) be provided to the user to alert the user that the sensor has entered into the second mode. However, it may not be necessary that the user take any action at that time. Providing a second mode or observe mode as described herein may provide significant benefits by decreasing the interaction required of a user as compared to currently available sensors by reducing unnecessary interactive maintenance. Depending upon the control software saved in memory system 104 of the sensor, the sensor, may, for example, change compensation, increase the frequency of pulse/electronic interrogation tests, measure one or more additional parameters, change the range of nominal sensor response, etc. in the second mode. Such action may, for example, be automated or not require user intervention.

In the case of a sensor in which a response to electronic interrogation is found to stabilize in the second mode (via, for example, electronic or electrical circuitry 100), that response may stabilize within the original range of nominal response or within a different or offset range of nominal response. One or more limits or thresholds for acceptable response/nominal response for a sensor may be defined. If a sensor stabilizes to a response range outsize of such a limit or threshold, the sensor may, for example, be flagged for service or replacement. In the case of sensor 10a(ii), the rate of change stabilizes, and the system predicts that the future state of sensor 10a(ii), while offset from the original range or nominal response, will be stable within a new, acceptable nominal range. The system may, for example, trigger a "recalibrate sensor" indication or alert and/or re-set the system in its new state. In the case of "new" calibration, the sensor may, for example, determine delta MPV from a new "anchor" value determined during the new calibration. The sensor may also (alternatively or additionally) continue to determine delta MPV from the calibration at the time of manufacture.

On the other hand, the data trace of sensor 10a(iii) indicates a catastrophic failure of sensor 10a(iii). Again, once the delta MPV exceeds the −3 sigma lower limit, the rate of change may, for example, be monitored over one or more time periods in the second mode to determine if the sensor's response to electronic interrogation becomes stable. In the case of sensor 10a(iii), the sensor response (delta MPV in this example) continues to rapidly change and the system predicts that sensor 10a(iii) will rapidly move out of its useful state for gas detection. The system may, for example, trigger a "replace sensor" alert. Having made such a determination, a quantitation may be performed, and an alert provided to take the sensor out of operation either permanently or for a period of time (for example, 24 hours or a number of days) if a repair is possible. One may replace the sensor during that time if the out of service period is excessively dangerous or burdensome.

"Group" nominal ranges of response to electronic interrogation may also be determined using a data distribution over a population of sensors (for example, a plurality of like sensors) which may, for example, share at least one common characteristic other than being a like sensor. As used herein, the term "like" refers to sensors manufactured in a similar or the same manner. In general, such sensors are manufactured to sense the same analyte and include a sensing component manufactured in the same manner. For example, like electrochemical gas sensor for a specific gas analyte may include working electrodes manufactured in a similar or same manner and include the same electrolyte. A counter electrode, a reference electrode and/or electronic circuitry of such sensors may also be manufactured in a similar or same manner. Such electrochemical gas sensor may, for example, be two- or three-electrode sensors as known in the art. Like combustible gas sensors may, for example, include a sensing element, a compensating element and/or electronic circuitry manufactured in a similar or the same manner.

With respect to a common characteristic (other than being a like sensor) the population of sensors may, for example, share the same local environment and/or a common range of manufacture date/time. Such sensors could be units all used at the same location of a particular customer or all units used in a larger area (a city or county for instance). The distribution could also, for example, be based on sensor manufacture date code and cover a global and/or a localized population. Groups and subgroups of like sensor may be established based upon differing shared or common characteristics. The results from each unit may be compiled, and the distribution of the entire population may be used as the nominal data set.

Figure 3:
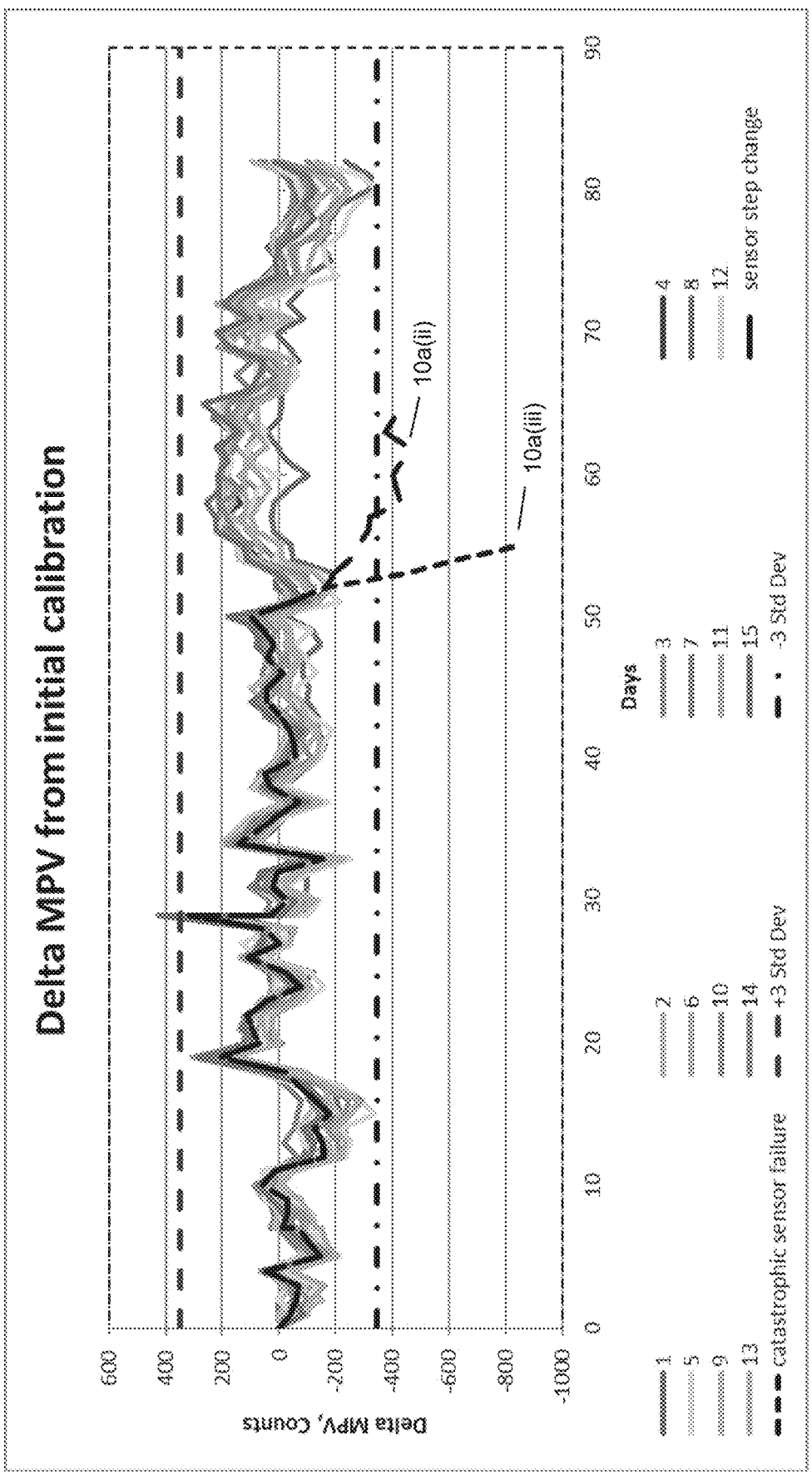
FIG. 3 illustrates the change, after initial calibration, in sensor response (MPV) to an electronic interrogations over time for multiple sensors.

FIG. 3 illustrates a representative example of data from 15 sensors in the same local environment. As described above, the change in MPV value from the initial calibration point is plotted for all sensors over 80+ days. The average over the 80+ days was 5 counts with a standard deviation of 117 counts. In the representative example of FIG. 3, group limits or thresholds may, for example, be established using a multiple of sigma. In the illustrated embodiment, group upper and lower thresholds were established using ±3 times the standard deviation to capture 99.7% of the nominal distribution. Group limits may, for example, be determined via a processor system external to the plurality of like sensors which is in communication with each of the plurality of like sensors to received data/information therefrom. The determined group limits may, for example, be transmitted from the external processing system to each of the plurality of like sensor. Such group limits are denoted by upper and lower dashed lines in FIG. 3. Once a measured delta MPV for a particular sensor moves to beyond these limits, the sensor system can enter a second mode or observe mode. As described above, in a number of embodiments, the rate of change of the delta MPV can be tracked for a sensor in the second mode to determine if sensor response will stabilize. Similar to FIG. 2, two examples are provided in FIG. 3 for a sensor step change (sensor $10a(ii)$) and a catastrophic sensor failure (sensor $10(iii)$). The actions for such individual sensors (for example, adjusting nominal thresholds or initiation of notifications/alerts such a "re-calibration alert" and a "replace sensor" alert) may, for example, be the same as described above in connection with the single sensor example of FIG. 2.

Figure 4:
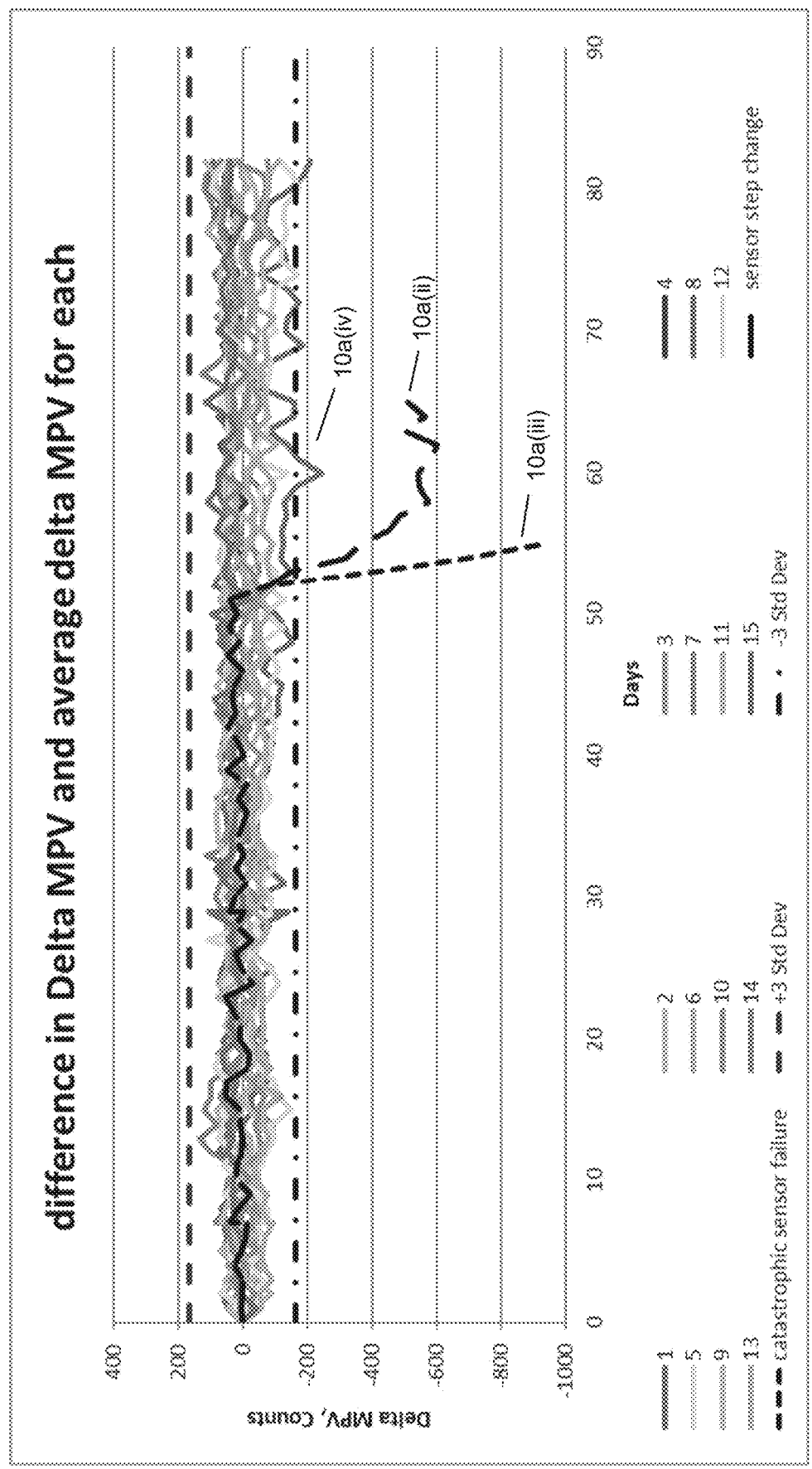
FIG. 4 illustrates the change, after initial calibration, in sensor response (set forth as the difference between a change in MPV and the average change in MPV) to an electronic interrogation over time for multiple sensors.

Referring again to FIG. 3, it is apparent that the studied local population of sensors responds in a similar manner to the day-to-day changes in the local environment. This result suggests an additional treatment using the local population data to compare each sensor's daily delta MPV value with the average daily delta MPV for all the sensors in that local population. In this way, the nominal behavior for the population is normalized for each interrogation event and deviations from nominal behavior are more apparent. FIG. 4 illustrates this methodology. The average over the 80+ days is 0 counts, but the standard deviation is now only 55 counts. Again, group limits can be established using ±3 times the standard deviation to capture 99.7% of the nominal distribution. These are denoted by the dashed traces in FIG. 4. This data treatment removes a portion of the day to day noise in the delta MPV value and makes the two deviation cases to become more easily discernible from the other sensors.

Figure 5:
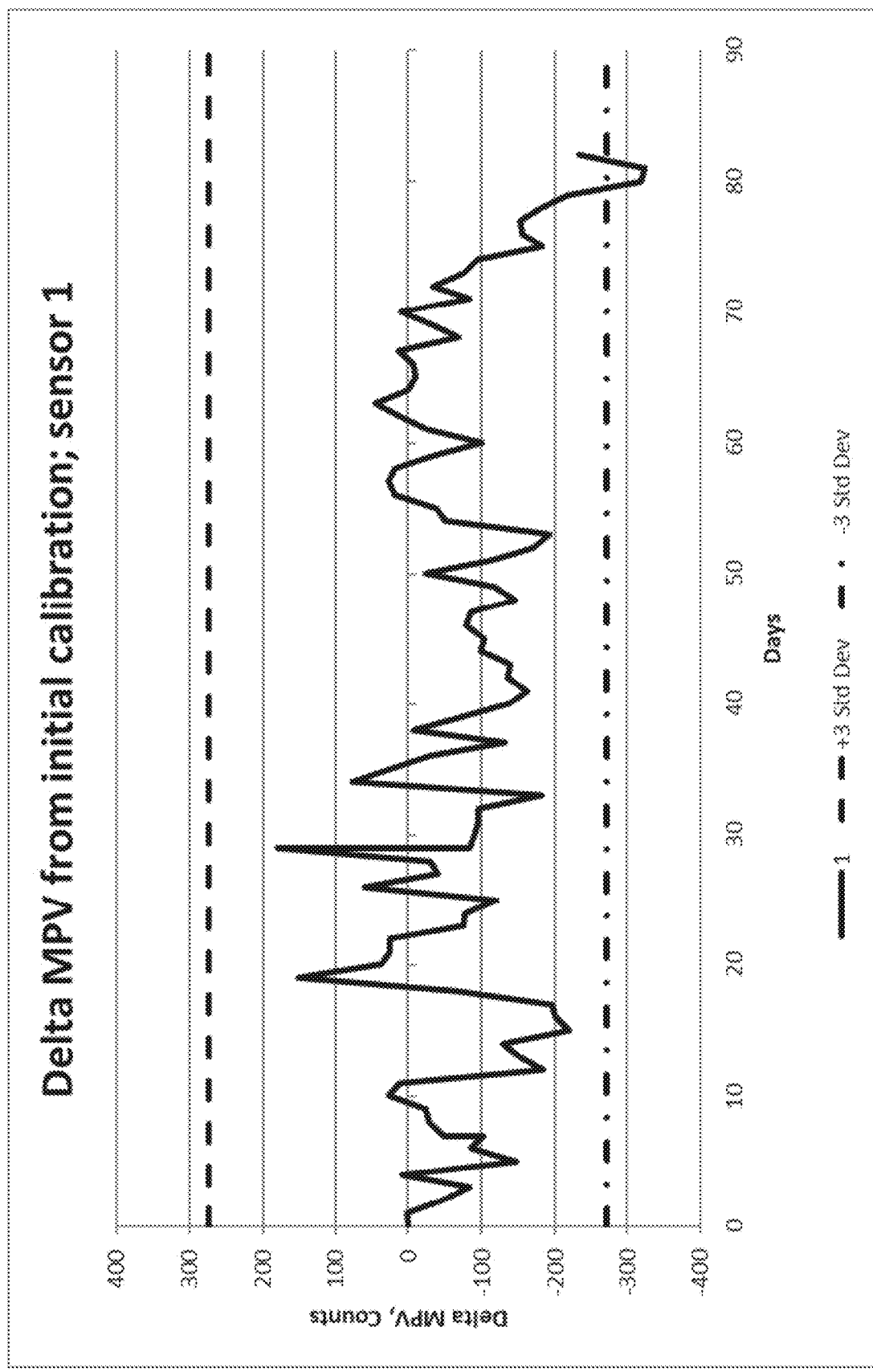
FIG. 5 illustrates the change, after initial calibration, in sensor response (MPV) to electronic interrogations over time for a single sensor which briefly drops below a threshold of −3 standard deviation but subsequently recovers.

Some sensors may exhibit more inherent noise than the general population. A sensor that is flagged by the population treatment discussed in connection with FIG. 3 (that is, upon comparison of the sensor response to one or more electronic interrogations to group limits or thresholds determined for the population/plurality of like sensors) may still be operating nominally when compared to its own history (that is, upon comparison of the sensor response to one or more electronic interrogations to individual limits or thresholds determined for the individual sensor). In light of that and other cases, the treatment discussed in connection with FIG. 3 can be combined with the single sensor treatment discussed in connection with FIG. 2. In the representative example of FIG. 4, sensor $10a(iv)$ shows a few instances of dropping below the −3 standard deviation/threshold line for the group/plurality of like sensors being monitored. Sensor $10a(iv)$ may, for example, be identified of flagged for a follow-up single treatment or evaluation. FIG. 5 illustrates a single sensor treatment (as described, for example, in connection with FIG. 2 above) for sensor $10a(iv)$. As illustrated in FIG. 5, sensor $10a(iv)$ briefly drops below the −3 standard deviation limit for the individual sensor but recovers. By combining both a group, population or distribution treatment and an individual sensor treatment as described herein, a more comprehensive evaluation is obtained and sensor $10a(iv)$ may, for example, be deemed to be functioning adequately.

Figure 6:
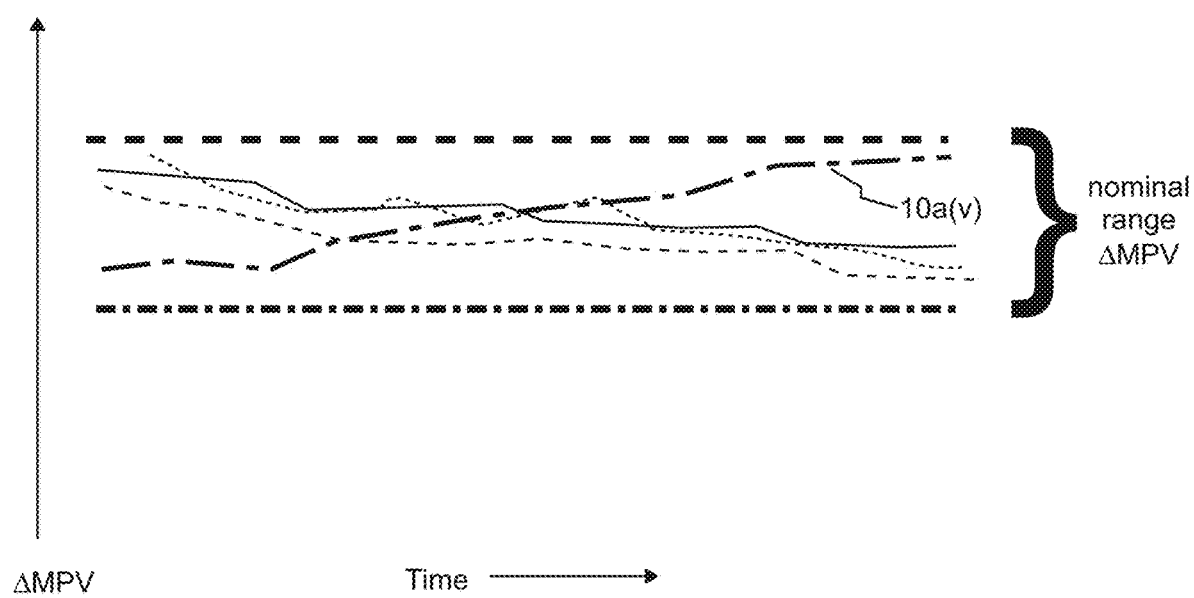
FIG. 6 illustrates the change, after initial calibration, in sensor response (set forth as the difference between a change in MPV and the average change in MPV) to an electronic interrogation over time for multiple sensors, wherein the output of one of the sensors is changing in a manner different from the others but its output is still in the nominal range.

When evaluating trends over a population of, for example, like sensors that share at least one common characteristic (that is, a common characteristic other than being a like sensor; for example, geographic location, manufacture date range, etc.) data analysis other than determination of whether a measured value is outside of a nominal range may be performed. One may, for example, expect (based upon data from a sensor population) that a particular sensor should be stabilizing or following a certain trend, but the particular sensor may be exhibit output that is different from its peers or other sensors in the monitored population. Such differences may, for example, be exhibited in manner other than output of a particular value/parameter (for example, MPV or delta MPV) outside of a threshold range (for example, outside+/−3 std. deviation). One may, for example, determine/analyze the magnitude of response, the magnitude of the rate of change and/or the direction of change of each sensor relative to peers. As illustrated in FIG. 6, sensor $10a(v)$ is exhibiting a rate of change in delta MPV that is opposite that of the other sensors in the studied population. Sensor $10a(v)$ may, for example, be identified or flagged and placed in a second or observe mode for further/alternative analysis and/or evaluation based on such a trend, which is different from its peers, even though the delta MPV behavior is within in the nominal range for the population of sensor and/or for individual sensor $10a(v)$.

In a number of embodiments, in the case that it is determined in the second mode that, for example, a particular sensor should be recalibrated and/or that its nominal range of response should be offset by at least a defined or predetermined amount from the nominal range of a population/plurality of like sensors of which the particular sensor is a member, it may, for example, be determined that the particular sensor should no longer be tracked as a member of the population/plurality of like sensors. If the particular sensor stabilizes within the nominal range of the population/plurality of like sensors or only slightly offset therefrom, it may, for example, be determined that the particular sensor should be continued to be tracked as a member of the population/plurality of like sensors and its response may continue to be considered in determining the group nominal thresholds for the population/plurality of like sensors.

In the case of monitoring population/plurality of like sensors, a sensor response or response trend different from its peers or other sensors in the monitored population/plurality of like sensors may not be an indication that the sensor at issue is malfunctioning but may be an indication that the sensor should not be a member of the monitored population/plurality of like sensors. Such a different response may, for example, result from a different microenvironment in a particular location. For example, the sensor of the monitored population/plurality of like sensor exhibiting a different response/trend may be located within a structure at a particular location, while the other sensors of the population/plurality of like sensors may be positioned out of doors. Similarly, the sensor of the monitored population/plurality of like sensor exhibiting a different response/trend may be located within direct sunlight while the other sensors of the population/plurality of like sensors are not. Thus, a response of a sensor that differs from that of its peers in a population/plurality of like sensor may trigger an investigation of whether the sensor in properly included in the population/plurality of like sensors. It may, for example, be determined that the sensor under investigation should be monitored only individually or within another population/plurality of like sensors.

In addition to providing further information/guidance in analyzing the response of one or more sensors, tracking the response to periodic electronic interrogations of a population/plurality of like sensors may, for example, provide information regarding a systemic issue with the sensors of the population/plurality of like sensors. Such sensors may, for example, have been manufactured in a determined date/time or manufacture code range. Certain defects (for example, a defect in electrolyte composition) may not be discovered at the time of manufacture but may result in anomalous response to electronic interrogations thereafter. Tracking of the response of such a plurality of like sensors to electronic interrogation may, for example, result in detection of a systemic problem with the sensors even before such a defect becomes otherwise apparent.

Changes in maximum peak value and/or one or more other parameter from the time of manufacture of a sensor (and/or from another starting or anchor point, such as a subsequent calibration) until later in a sensor's life may be analyzed to, for example, determine what type of environmental conditions the sensor has experienced over that historical period (for example, low humidity or drying conditions). Based on such historical data, one may change one or more parameters of sensor operation. A software algorithm stored in memory and executable by one or more processors may, for example, apply a different temperature compensation. An algorithm may, for example, apply a different sensitivity compensation based on such historical data. An algorithm hereof (based on such historical data) may, for example, be used to alter nominal response range based on such historical data.

Data from sensors that that are not like sensors or sensors that have very different characteristics than one or more sensors being monitored/analyzed may also be used in determining the operational status of the sensor(s) in the devices, systems and methods hereof. Such sensors that are not like sensors may, for example, be sensors that are for an analyte other than the sensor(s) for which the operational status is being determined. Such sensors that are not like sensors may, for example, be a different type of sensor (for example, a combustible gas sensor in the case that the like sensors are electrochemical gas sensors).

Moreover, sensors for environmental conditions such as pressure sensors, humidity sensors, altitude sensors or altimeters, etc. may also or alternatively be used in determining operational status. Data from temperature and/or humidity sensors may, for example, be used in determining appropriate nominal ranges for a measured parameter (for example, delta MPV as described in representative examples hereof). Different settings may be established for sensor locations that are cold and dry than those that are hot and humid. Altitude may, for example, be related to an oxygen concentration which affects the output of oxygen sensors as well as combustible gas sensors. At high altitude, the concentration of oxygen is lower than at sea level (fewer molecules of oxygen are present per unit volume). Below sea level, for example, in an underground mine, the environment may be rich in oxygen.

For example, in the case the operational status of one or more combustible gas sensors is being tracked under a methodology hereof, an oxygen sensor may be used to determine the combustible gas sensor(s) is/are operating in a condition of oxygen deficiency or oxygen excess over a particular time period. Such an oxygen sensor may, for example, be an electrochemical gas sensor. Likewise, sensors for inhibitors and/or poisons for combustible gas sensors (for example, sulfur-containing compounds, halogens, silicon-containing compounds etc.) may be sensed by, for example, electrochemical and/or other sensors.

In the case the operational status of one or more electrochemical gas sensors is being tracked under a methodology hereof, a combustible gas sensor or other sensor may, for example, be used to detect interferent gases for the electrochemical gas sensor(s). Alcohols may, for example, be detected via a combustible gas sensor. Speciation, as disclosed, for example, U.S. Pat. No. 10,234,412, the disclosure of which is incorporated herein by reference, may be used in detecting a species of alcohol. Alcohols may affect certain electrochemical gas sensor such as carbon monoxide or CO sensors. Even a small increase in a combustible gas sensor output may be associated in time with anomalous output from an electrochemical gas sensor for CO sensor or even with such a sensor going offline. Alkenes may also be detected via combustible gas sensors. Alkenes are similarly interferents for electrochemical gas sensors for CO. Using data from one or more combustible gas sensors, one may determine if an alkene us present which is causing a response in one or more CO sensors.

The timespan of history or data from one or more gas sensors, pressure sensors, humidity sensors, temperature sensors etc. may be analyzed to determine how such a data history may be affecting the performance of one or more sensor monitored under the methodologies hereof. Location data (for example, from GPS or other systems) and the location of a monitored sensor or sensors in a facility may, for example, be correlated with gas test data, anomalies, alarms, up-scale readings, down-scale readings etc. Determination and/or analysis of nonstandard conditions or occurrences can be associated with the output of a monitored sensor or sensors.

Various types of gas sensors may include one or more filters to, for example, limit or prevent gas sensing elements from coming into contact with or being exposed to an inhibitor, poison, interferent etc. Changes in the transport properties of such filters upon exposure to such an inhibitor, poison, interferent etc. may affect sensor response. Sensors sensitive to an inhibitor, poison, interferent etc. for a sensor or sensors being monitored using a methodology hereof may, for example, be used in interpreting output trends in such sensor(s). Likewise, such sensors sensitive to an inhibitor, poison, interferent etc. may be used to monitor or track the operational status of a filter for a sensor or sensors being monitored using a methodology hereof.

Figure 7:
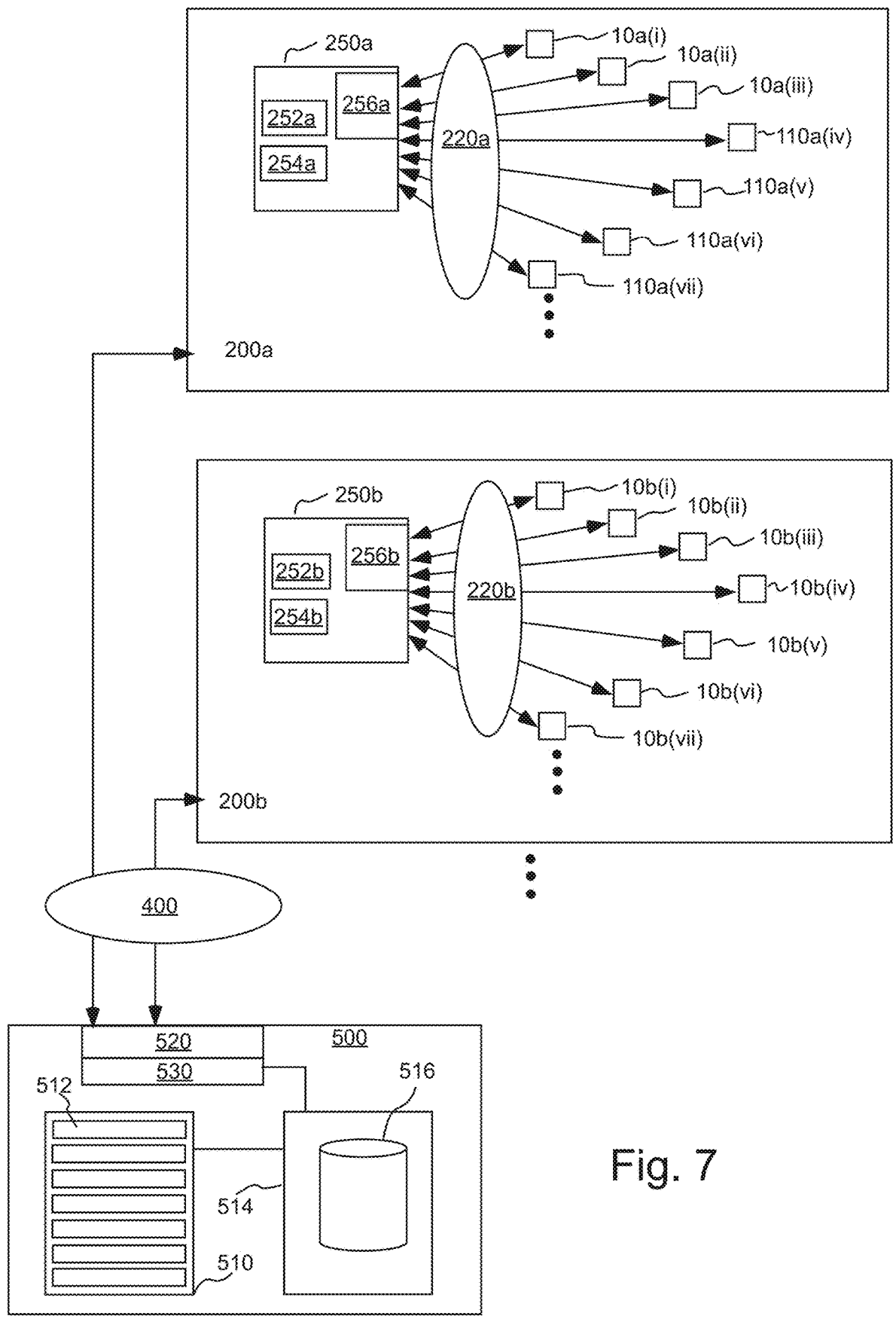
FIG. 7 illustrates a representative embodiment of a system for data communication, processing and analysis for sensor data from one or more facilities or locations.

FIG. 7 illustrates a representative embodiment of a system for collection, communication and analysis of data from one or multiple sensors which may, for example, be located at a single facility or distributed over multiple facilities. In a number of embodiments hereof, a facility 200a (for example, an oil refinery, off-shore drilling rig, manufacturing facility, industrial chemical plant etc.) includes one or more sensor 10a(i) through 10a(vii) hereof, while one or more other facilities represented by facility 200b includes one or more other sensors 10b(i) through 10b(vii) hereof. Although seven sensors are illustrated in each of facilities 200a and 200b, facilities may include fewer or more sensors. Some facilities may, for example, include 100 or more sensors. Operation of the system components of facility 200b (and/or other facilities) with respect to data collection, communication and/or processing is very similar to the components of facility 200a. Data communication and/or processing in the systems hereof is, therefore, primarily discussed below in connection with facility 200a.

As described above each sensor 10a(i) hereof includes a communication system (for example, transceiver) which may be wired or wireless. Data from sensors 10a(i) through 10a(vii) may, for example, be communicated directly to a remote processing system 500, which is discussed further below. Data from sensors 10a(i) through 10a(vii) may alternatively be transmitted to remote system 500 via a local system 250a. In a number of embodiments, data may, for example, be communicated from sensors 10a(i) through 10a(vii) to local system 250a via local network 220a which may, for example, include a 4 to 20 milliamp (mA) transmission system as known in the art, an ethernet-based network, and/or a wireless network. Data may, for example, be collected and transmitted in real-time to remote system 500 for analysis. Data transfer may be performed in a continuous or a discontinuous/batch manner. For example, raw sensor data or processed sensor data may be transmitted by local system 250a to remote system 500 for processing (or further processing) and/or analysis by remote system 500. Remote system 500 can received data from many local systems 250a, 250b etc. (that is, from many different facilities). Local system 250a may, for example, include a processing system 252a (including, for example, one or more processors or microprocessors), an associated memory system 254a in communicative connection with processor system 252a and a communication system 256a in communicate connection with processor system 252a. Processing/analysis may, for example, be distributed in the processing systems of the sensors, the local systems and remote system 500 (for example, in determining group upper thresholds and lower thresholds). Transmission from sensors 10a(i) through 10a(vii) and/or local system 250a to remote system 500 occur through a network 400 which may include wired and/or wireless communication protocols (for example, via cell phone transmission protocols, internet transmission protocols, data via telephone wire protocols etc.)

Remote system 500 may, for example, include a central processing system or a distributed processing system that may, for example, include one or more computers, servers or server systems 510. Computer(s), server(s) or server system (s) 510 may, for example, include one or more processors or processor systems 512 which are in communicative connection with one or more memory or storage systems 514 as known in the computer arts. Memory system(s) 514 may include one or more databases 516 stored therein. Local systems 250a, 250b etc. may communicate with a communication system or systems 520 of remote system 500 through one or more wired or wireless communication channels 400 (for example, landline telephones, wireless telephones, a broadband internet connection and/or other communication channel(s)) as described above. Software stored in memory system(s) 514 or in one or more other memory system in communicative connection with processor(s) 512 may be used to process or analyze data from local systems 250a, 250b etc.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of operating a gas sensor in a gaseous environment to detect a gas analyte, the gas sensor including a sensing component, the method comprising:
   in a first mode, during a period of operation of the gas sensor for detection of the gas analyte, interrogating the sensor by periodically applying a first-mode electrical signal to the sensing component of the sensor, measuring a sensor response to the first-mode electrical signal which is indicative of a sensitivity of the sensor each time the first-mode electrical signal is applied to the sensing component,
   analyzing the sensor response to the periodically applied first-mode electrical signals in the first mode to determine whether at least one of one or more thresholds has been exceeded based upon the sensor response determined each time the first-mode electrical signal is applied to the sensing component in the first mode,
   entering a second mode if the at least one of the one or more thresholds has been exceeded in the first mode,
   during a period of operation of the gas sensor for detection of the gas analyte in the second mode, periodically applying a second-mode electrical signal to the sensing component of the sensor,
   measuring a sensor response to the second-mode electrical signal which is indicative of the sensitivity of the sensor each time the second-mode electrical signal is applied to the sensing component, and
   analyzing the sensor response to the periodically applied second-mode electrical signals in the second mode differently from the analysis of the sensor response to the periodically applied first-mode electrical signals in the first mode to determine if the sensor response to the periodically applied second-mode electrical signals in the second mode is stabilizing.

2. The method of claim 1 further comprising determining a rate of change of the sensor response during the second mode to determine if the sensor response to the periodically applied second-mode electrical signals is stabilizing.

3. The method of claim 2 wherein at least one of a magnitude and a direction of the rate of change of the sensor response to the periodically applied second-mode electrical signals is determined.

4. The method of claim 2 wherein the sensor is an electrochemical gas sensor and the sensing component is a working electrode of the electrochemical gas sensor.

5. The method of claim 4 wherein a value for the sensor response to the periodically applied first-mode electrical signals is determined on the basis of at least one defined parameter of the sensor response and the sensor response to the periodically applied second-mode electrical signals is determined on the basis of at least one defined parameter of the sensor response.

6. The method of claim 5 wherein the at least one defined parameter of the sensor response to the periodically applied first-mode electrical signals and the at least one defined parameter of the sensor response to the periodically applied second-mode electrical signals is selected independently from the group of a maximum current peak value, an area under a current curve, a minimum peak value, a peak-to-peak value, a reverse area under the curve, a baseline value or a function of one or more thereof.

7. The method of claim 5 wherein the value for the sensor response at each of the periodically applied first-mode electrical signals is a change in the value of at least one defined parameter of the sensor response measured at each of the periodically applied first mode electrical signals from a value thereof determined at a calibration of the sensor.

8. The method of claim 4 wherein the one or more thresholds for the sensor response to the periodically applied first-mode electrical signals are determined by tracking a value of the sensor response to the periodically applied first-mode electrical signals over time and determining an upper threshold and a lower threshold of nominal behavior for the sensor.

9. The method of claim 4 wherein the one or more thresholds for the sensor response to the periodically applied first-mode electrical signals are determined by tracking the sensor response to the periodically applied first-mode electrical signals over time for a plurality of like sensors operating concurrently with the sensor to detect the gas analyte and determining a group upper threshold and a group lower threshold of nominal behavior for the plurality of like sensors.

10. The method of claim 9 wherein one or more other thresholds are determined by contemporaneously tracking the sensor response to the periodically applied first-mode electrical signals of each of the plurality of like sensors comprising the sensor over time and determining an individual upper threshold and an individual lower threshold of nominal behavior for each of the plurality of like sensors.

11. The method of claim 9 wherein each of the plurality of like sensors has at least one common characteristic other than being a like sensor.

12. The method of claim 11 wherein the at least one common characteristic is a geographical area of deployment or a range of time of manufacture.

13. The method of claim 1 further comprising changing the one or more thresholds after determining that the sensor response to the periodically applied second-mode electrical signals has stabilized.

14. The method of claim 1 wherein the sensor response to the periodically applied first-mode electrical signals and the sensor response to the periodically applied second-mode electrical signals is determined without application of a test gas to the sensor.

15. The method of claim 1 wherein there are a plurality of thresholds for the sensor response to the periodically applied first-mode electrical signals and two of the plurality of thresholds are determined by tracking a value of the sensor response to the periodically applied first-mode electrical signals over time and determining an upper threshold and a lower threshold of nominal behavior for the sensor.

16. The method of claim 1 wherein there are a plurality of thresholds for the sensor response to the periodically applied first-mode electrical signals and two of the plurality of thresholds are determined by contemporaneously tracking the sensor response to the periodically applied first-mode electrical signals over time for a plurality of like sensors and determining a group upper threshold and a group lower threshold of nominal behavior for the plurality of like sensors.

17. The method of claim 16 wherein two others of the plurality of thresholds are determined by tracking the sensor response to the periodically applied first-mode electrical signals of each of the plurality of like sensors over time and determining an individual upper threshold and an individual lower threshold of nominal behavior for each of the plurality of like sensors.

18. The method of claim 1 wherein data from the sensor is transmitted to a remote processor system for analysis.

19. The method of claim 1 wherein data from a second gas sensor for a second gas analyte different from the gas analyte or data from a third sensor for an environmental condition is transmitted to the gas sensor, and the method further includes analyzing at least one of the data from a second gas sensor or the data from third sensor for an environmental condition to determine an operational status of the gas sensor.

20. A method of operating a gas sensor in a gaseous environment to detect a gas analyte, the gas sensor including a sensing component, the method comprising:
  in a first mode, during a period of operation of the gas sensor for detection of the gas analyte, interrogating the sensor by periodically applying a first-mode electrical signal to the sensing component of the sensor, measuring a sensor response to the first-mode electrical signal which is indicative of a sensitivity of the sensor each time the first-mode electrical signal is applied to the sensing component,
  analyzing the sensor response to the periodically applied first-mode electrical signals in the first mode to determine whether one of a plurality of thresholds has been exceeded based upon the sensor response determined each time the first-mode electrical signal is applied to the sensing component in the first mode, wherein two thresholds for the sensor response to the periodically applied first-mode electrical signals are determined by contemporaneously tracking the sensor response to the periodically applied first-mode electrical signals over time for a plurality of like sensors and determining a group upper threshold and a group lower threshold of nominal behavior for the plurality of like sensors, and wherein two others of the plurality of thresholds are determined by tracking the sensor response to the periodically applied first-mode electrical signals of each of the plurality of like sensors over time and determining an individual upper threshold and an individual lower threshold of nominal behavior for each of the plurality of like sensors,
  entering a second mode for each of the plurality of like sensors independently if at least one the plurality of thresholds is exceeded in the first mode based upon a comparison of the sensor response to the periodically applied first-mode electrical signals of each of the plurality of like sensors to the group upper threshold and the group lower threshold as well as to the individual upper threshold and the individual lower threshold,
  during a period of operation of the gas sensor for detection of the gas analyte in the second mode, periodically applying a second-mode electrical signal to the sensing component of the sensor, and analyzing the sensor response to the periodically applied second-mode electrical signals in the second mode differently from the analysis of the sensor response to the periodically applied first-mode electrical signals in the first mode, to determine if the sensor response to the periodically applied second-mode electrical signals in the second mode is stabilizing.

21. The method of claim 20 wherein the sensor is an electrochemical gas sensor and the sensing component is a working electrode of the electrochemical gas sensor and the method further comprises determining a rate of change of the sensor response during the second mode to determine if the sensor response to the periodically applied second-mode electrical signals is stabilizing.

22. A system, comprising:
a sensor comprising a sensing component having at least one property sensitive to a gas analyte in a gaseous environment; and
circuitry in operative connection with the sensing component configured in a first mode to interrogate the sensor by periodically applying a first-mode electrical signal to the sensing component during a period of operation of the sensor for detection of the gas analyte, measuring a sensor response to the first-mode electrical signal which is indicative of a sensitivity of the sensor each time the first-mode electrical signal is applied to the sensing component, analyze the sensor response to the periodically applied first-mode electrical signals in the first mode to determine, based upon the comparison of sensor response to the periodically applied first-mode electrical signals to one or more thresholds, whether to enter a second mode, if at least one of the one or more thresholds are exceeded, the circuitry further being configured to periodically apply a second-mode electrical signal to the sensing component of the sensor during a period of operation of the sensor for the detection of the gas analyte in the second mode, measure a sensor response to the second-mode electrical signal which is indicative of the sensitivity of the sensor each time the second-mode electrical signal is applied to the sensing component, and analyze the sensor response to the periodically applied second-mode electrical signals in the second mode differently from the analysis of the sensor response to the periodically applied first-mode electrical signals in the first mode to determine if the sensor response to the periodically applied second-mode electrical signals in the second mode is stabilizing.

23. A method of operating a system including a plurality of like gas sensors, each of the plurality of like gas sensors including a sensing component to detect a gas analyte in a gaseous environment, comprising:
in a first mode, interrogating each of the plurality of like gas sensors during a period of contemporaneous operation of the plurality of like gas sensors to detect the gas analyte by periodically applying a first-mode electrical signal to the sensing component of the sensor, determining a sensor response to the first-mode electrical signal which is indicative of a sensitivity for each of the plurality of like gas sensors each time the first-mode electrical signal is applied to the sensing component thereof, and independently analyzing the sensor response of each of the plurality of like gas sensors to the periodically applied first mode electrical signals based upon a group nominal response of the plurality of like gas sensors to the periodically applied first-mode electrical signals determined over time.

24. The method of claim 23 further comprising determining whether to enter a second mode independently for each of the plurality of like gas sensors based upon comparison of the sensor response to the first-mode electrical signal of each of the plurality of like gas sensors to the group nominal response of the plurality of like gas sensors in the first mode, periodically applying a second-mode electrical signal to the sensing component of one of the plurality of like gas sensors determined to be outside of the group nominal response of the plurality of like gas sensors in the second mode during a period of operation of the one of the plurality of like gas sensors to detect the gas analyte, and analyzing the sensor response to the second-mode electrical signal of the one of the plurality of like gas sensors to the periodically applied second-mode electrical signals in the second mode differently from the analysis of the sensor response to the periodically applied first-mode electrical signals in the first mode to determine if the sensor response to the periodically applied second-mode electrical signals in the second mode is stabilizing.

* * * * *